(12) United States Patent
Magidson et al.

(10) Patent No.: US 10,441,469 B2
(45) Date of Patent: Oct. 15, 2019

(54) CORDED EARPLUG

(71) Applicant: MOLDEX-METRIC, INC., Culver City, CA (US)

(72) Inventors: Mark Magidson, Los Angeles, CA (US); Crest Turdjian, Los Angeles, CA (US); Fred Ryan, Los Angeles, CA (US)

(73) Assignee: MOLDEX-METRIC, INC., Culver City, CA (US)

( * ) Notice: Subject to any disclaimer, the term of this patent is extended or adjusted under 35 U.S.C. 154(b) by 1387 days.

(21) Appl. No.: 14/273,299

(22) Filed: May 8, 2014

(65) Prior Publication Data

US 2014/0246029 A1    Sep. 4, 2014

Related U.S. Application Data

(63) Continuation of application No. 13/066,871, filed on Apr. 26, 2011, now abandoned.

(51) Int. Cl.
*A61F 11/08* (2006.01)
*A61F 11/12* (2006.01)

(52) U.S. Cl.
CPC .............. *A61F 11/08* (2013.01); *A61F 11/12* (2013.01); *Y10T 29/49826* (2015.01)

(58) Field of Classification Search
CPC ........................... A61F 11/08; A61F 2011/085
USPC ........ 128/846, 857, 864–867; 181/130, 135; 381/380; D24/106
See application file for complete search history.

(56) References Cited

U.S. PATENT DOCUMENTS 5,711,313 A * 1/1998 Fleming .................. A61F 11/08
128/864
6,938,622 B2 * 9/2005 Huang .................... A61F 11/12
128/864

* cited by examiner

*Primary Examiner* — Ophelia A Hawthorne
*Assistant Examiner* — Caitlin A Carreiro
(74) *Attorney, Agent, or Firm* — Charles H. Schwartz

(57) ABSTRACT

An apparatus and a method of making a corded earplug, including a flexible cord material having a particular cross-section. An earplug having a nose portion for insertion into the ear and a handle portion extending from the nose portion and lying outside of the ear when the nose portion is inserted into the ear. The handle portion including at least two openings physically displaced from each other. At least one of the openings extends within the handle portion and with at least one of the openings having a cross-section different than the cross-section of the cord material. An end portion of the flexible cord material is inserted into the at least one opening extending within the handle portion. The end portion of the flexible cord material is then inserted into the other opening in the handle portion so that the end portion of the flexible cord material is frictionally engaged along its length to lock the flexible cord material to the rear portion of the earplug because of the difference in cross-section between the cord and the at least one opening having a cross-section different than the cross-section of the cord material.

20 Claims, 2 Drawing Sheets

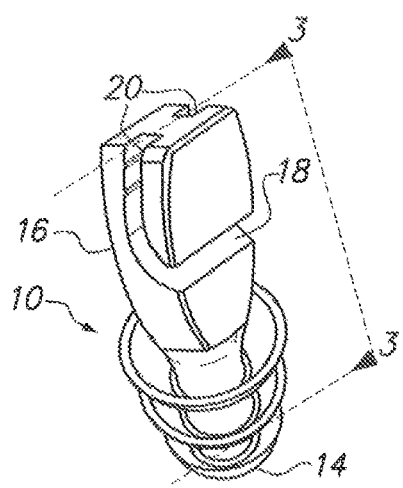
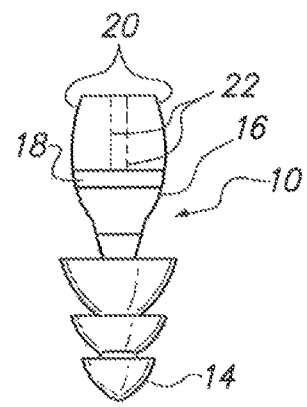
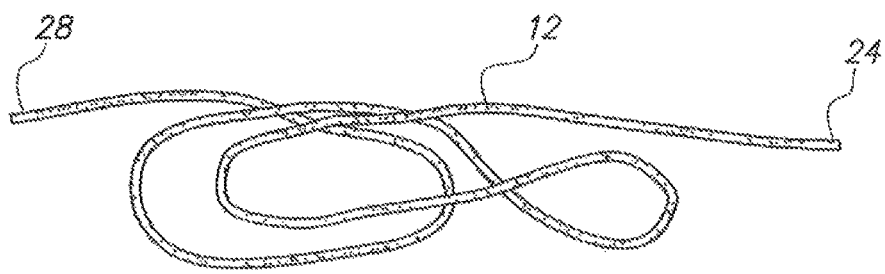
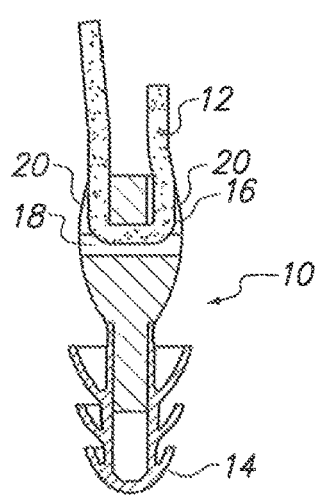
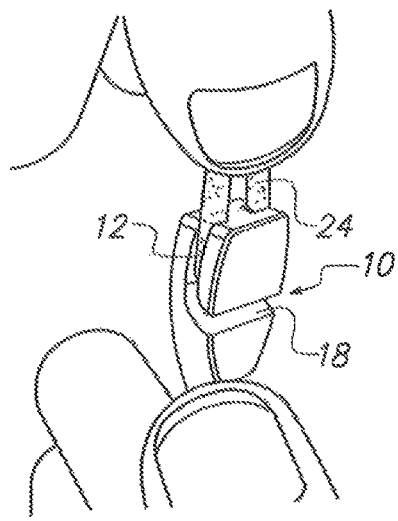
FIG. 1
FIG. 2
FIG. 4
FIG. 3
FIG. 5

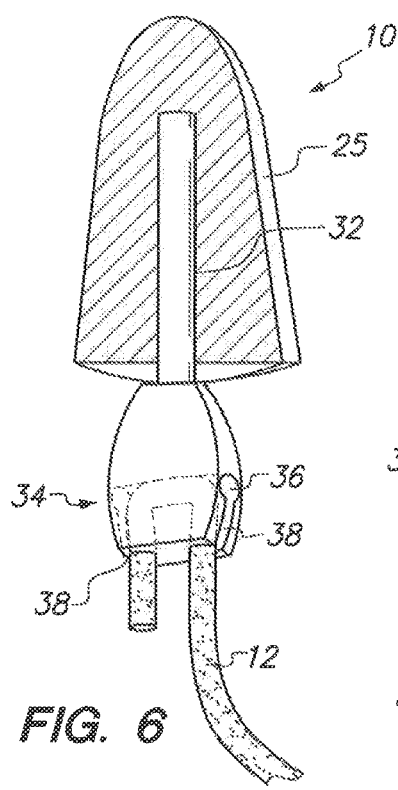
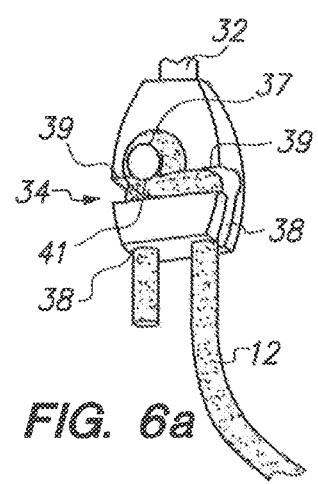
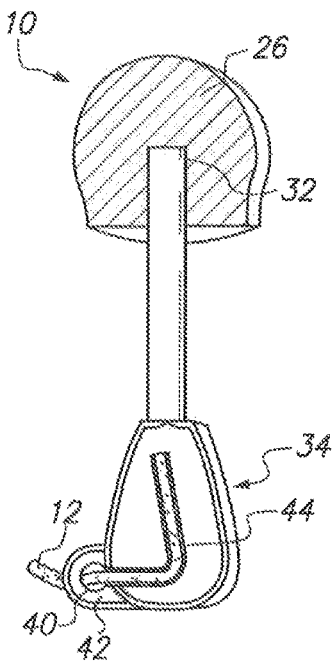
FIG. 6   FIG. 6a   FIG. 7
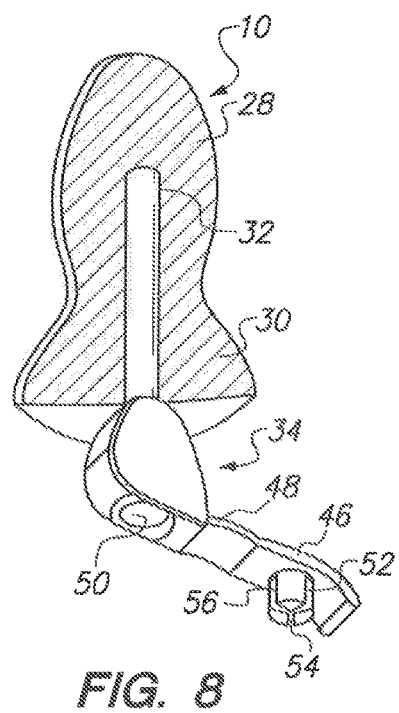
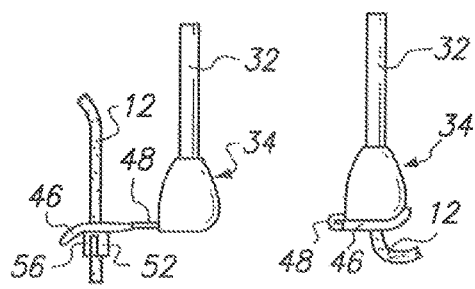
FIG. 8   FIG. 9a   FIG. 9b

CORDED EARPLUG

This Continuation Application is based on U.S. application Ser. No. 13/066,871 filed on Apr. 26, 2011 by Mark Magidson, et al., for Corded Earplug

BACKGROUND OF THE INVENTION

The present invention relates to a corded earplug and additionally to a method for making such a corded earplug.

In the prior art, corded earplugs are generally made by initially making an earplug by any conventional technique. The earplugs are either produced with an elongated opening at one end or an elongated opening is made at one end of the earplug after it has been produced. An adhesive is then applied to the opening and one end of a cord is inserted into the elongated opening, during the short time that the adhesive is liquid. This adhesive then bonds the cord within the opening at one end of the earplug and generally a pair of such earplugs is located at opposite ends of the cord. This produces the conventional type of corded earplug, which includes a number of additional steps after the earplugs are produced.

The difficulty with prior art corded earplugs is that it is difficult to insert the cord into the opening during the short period of time that the adhesive is liquid. In addition this method of attaching the cord to the earplug can result in a bond that is completely dependent on the adhesive and therefore may not be very strong. Also this method is permanent and does not allow for the pair of earplugs to be used without a cord. Other prior art corded earplugs use a cord with ends that can be inserted into an opening in the earplugs but are easily removable desired so that the earplugs can be used without the cord. Since the attachment of the cord to the earplugs is easily removable, the earplugs can be disengaged from the cord when this is not desired.

It would therefore be desirable to provide for a method of attaching a cord to an earplug using a method and apparatus that is simpler than the prior art and also produces strong connection between the cord and the earplug. In a prior application Ser. No. 12/924,462, filed Sep. 28, 2010, a method and apparatus fix overcoming the problems of the prior art were shown. This improved method and apparatus would work best if the cord was braided and included stiff end portions but, if the cord were a smooth plastic or a braided material without stiff end portions, then it would be more difficult to use the method and apparatus of this prior application.

SUMMARY OF THE PRESENT INVENTION

The present invention is an improvement to the prior application Ser. No. 12/924,462 and is directed to a corded earplug, and specifically to a method of making a corded earplug including providing a flexible cord material and a pair of earplugs. Each earplug has a nose portion for insertion into the ear and a rear portion extending from the nose portion and lying outside of the ear. Each rear portion of each earplug has a pair of openings physically displaced from each other and/or angularly displaced from each other. At least a first one of the openings extends within the rear portion. A end portion of the flexible cord material is inserted into the at least first one opening and then the end portion is inserted into the second other opening to have the end portion of the flexible cord material physically displaced and/or angularly displaced along its length to lock the flexible cord material to the rear portion of the earplug.

In the improvement of the present invention, at least one of the openings includes a channel extending outward from the opening to create a slot for receiving the cord. In this way the cord may be pulled through the slot into the at least one opening. The at least one opening is different in cross-section than the cord so that the cord, when pulled through the slot into the opening, is held in the at least one opening by friction.

Because of this technique, the cord itself loops around to produce a very strong attachment to the rear of the earplugs. However, if desired, the technique can be reversed by first removing the end of the cord from, the second opening and then pulled through the first opening to detach the cord from the earplug.

The present invention can be used with any type of earplug, such as a molded foam type or an earplug made out of a resilient elastomeric rubber-like material. The cord itself can be made of a braided material similar to a shoelace or from an elastomeric rubber-like material and if made of a braided material similar to a shoelace it mayor may not include a stiff end portion common on most shoelaces.

BRIEF DESCRIPTION OF THE DRAWINGS

FIG. 1 illustrates a perspective view of an earplug that can be removable attached to a cord or used without a cord using a first embodiment of the invention.

FIG. 2 illustrates a front view of the earplug of FIG. 1,

FIG. 3 illustrates a side cross-sectional view of the earplug of FIG. 1 taken along lines 3-3 of FIG. 1, FIG. 4 illustrates a cord for producing a corded earplug using a pair of earplugs of FIG. 1, FIG. 5 illustrates the technique of attaching the cord of FIG. 4 to the earplug of FIG. 1, FIG. 6 illustrates a perspective view of a different type of earplug that can be removable attached to a cord or used without a cord using a second embodiment of the invention, FIG. 6a illustrates a perspective view of an alternative structure for this second embodiment, FIG. 7 illustrates a perspective view of a different type of earplug that can be removable attached to a cord or used without a cord using a third embodiment of the invention.

FIG. 8 illustrates a perspective view of a different type of earplug that can be removable attached to a cord or used without a cord using a fourth embodiment of the invention, and FIGS. 9a and 9b illustrate the technique of attaching the cord of FIG. 4 to the carping of FIG. 8.

DETAILED DESCRIPTION OF THE DRAWINGS

As in FIGS. 1-3, an earplug 10 is shown and wherein a pair of earplugs 10 may be located at the ends of a flexible cord 12 shown in FIG. 4. The present invention can be incorporated with any type of earplug, such as a molded foam type or an earplug made out of a resilient elastomeric rubber-like material. The earplug may be a flanged type earplug such as shown in FIGS. 1-3 or may be an un-flanged type of earplug as shown in FIGS. 6-8.

In general, all earplugs have a nose portion 14 and a rear portion 16. The nose portion 14 is for insertion into the ear and the rear portion 16 forms a handle and extends from the nose portion and lies outside of the ear. In the present invention, the rear handle portion 16 also is formed with a cord attachment apparatus that includes a plurality of openings 18 and 20 that are physically displaced from each other and angularly displaced from each other. The opening 18 is formed as a slot and extends in a horizontal direction into the earplug 10 and the openings 20 each extends in a vertical direction on either side of the rear portion 16 of the earplug 10. At least one of the openings 20 is formed as a channel extending outward from the opening to create a slot for receiving the cord. In this way the cord may be pulled through the slot into this at least one opening 20.

The embodiment of FIGS. 1-3 shows the use of a pair of openings 20 but it will be appreciated that a single opening 20 may be used on one side of the rear portion 16 as will be seen with other embodiments of the invention. The major criteria for either one or both of the openings 20 is that at least one opening 20 is smaller in cross-section than the cord 12 so that the cord, when pulled or passed through the opening 18 and pulled into at least one of the openings 20, the cord 12 is held in the at least one of the openings 20 by friction. At least one of the openings 20 may also include ridges, as shown, to increase the frictional engagement between the cord 12 and the walls of at least one of the openings 20. The combination of the change in direction or looping of the cord 12 from the opening 18 to at least one of the openings 20 also helps to retain the cord 12 at the rear of the carping 10.

In the example shown in FIGS. 1-3, the opening 18 is angularly displaced 90 degrees from the pair of openings 20 but it will be appreciated that the angular relationship can be zero degrees to one hundred eighty degrees as long as there is a physical frictional relationship between the cord 12 and at least one of the openings. As one example, the rear portion 16 can have the opening 18 can pass through the rear portion 16 in a vertical direction. This can be seen in FIG. 2 by the dotted lines 22 that represent an opening passing through the rear portion 16 and then into either of the opening 20 in a vertical direction so there is substantially no angular displacement between the openings.

The cord 12 may be formed of a smooth plastic or may be formed of the cord 12 to support the earplugs 10 is a useful feature. The earplugs can be inserted into the ear and then removed and with the cord draped around the neck to keep the earplugs located with user without having to store the earplugs in some other place. The cord 12 has end portions 24 that can be a continuation of the cord material as shown in FIG. 4 or can be more rigid that the remaining length of the cord.

FIG. 5 illustrates the method of attaching the cord 12 to the rear handle portion 16 of the earplug, 10. As shown, one end portion 24 of the cord 12 is first passed through the opening 18 in the rear handle portion 16 and then pulled up to be inserted into one or more of the openings 20 in the rear handle portion 16 of the earplug 10 to be held by friction and also to form a loop portion of the cord 10. The end of the cord 12 is now firmly attached to the rear handle portion 16 of the earplug 10 and if a pulling force is applied to an outside portion of the cord 12 the cord will be held in place by the friction and looping of the cord. To remove the cord 12 from the rear portion 16 of the earplug 10 the above steps are reversed. The end portion 24 of the cord 12 is removed from the openings 20 and the cord 12 is then pulled through the opening 18.

FIGS. 6, 6a, 7 and 8, illustrate alternative earplug structures 10 that may be used with the cord attachment apparatus of the present invention and also give further embodiments of the cord attachment apparatus. It will be appreciated that anyone of the cord attachment apparatus of the present invention may be used with any type of earplug and the different earplugs shown in FIGS. 1-3 and 6-8 are only illustrative.

In FIGS. 6, 7 and 8, the earplug construction uses a soft, resilient polymeric foam body each comprising a smoothly contoured, homogenous, viscoelastic main body element adapted in size and shape to be inserted into the human ear canal. In FIG. 6, the main body element has a bullet shape 25 and in FIG. 7 the main body element has a hemispheric pod shape 26. In FIG. 8, the main body element has an elongated bulbous curved shape 28 including a flange portion 30.

All of the earplugs 10 in FIGS. 6-8 are supported on a stern member 32. The stern member 32 is an elongated member that may be tubular or solid throughout its cross section and may be uniform or non-uniform along its length. In a preferred structure, the elongated stern has two ends, one end is located in and secured to the interior of the main body of the earplug 10. The stern 32 then extends axially and outward from the carping 10 and the other end of the stern terminates at a point exterior to or adjacent to the base end of the earplug 10 and forms a handle portion 34 of the stern 12. The stem is sufficiently stiff so as to allow manipulation of the main body of the earplug 10 so that the earplug can be seated in the ear canal for maximum attenuation.

In FIG. 6, the handle portion 34 is a variation of the cord attachment design shown in FIGS. 1-3. Instead of the opening formed as the slot 18, in FIG. 6 the one opening 36 is formed as a hole extending through the handle portion and with openings 38 formed as a slot in the same manner as the openings 20 in FIGS. 1-3. In particular, either one or both of the openings 38 is smaller in cross-section than the cord 12 so that the cord, when passed through the opening 36 and pulled into at least one of the openings 38, the cord 12 is held in the at least one of the openings 38 by friction. The combination of the change in direction or looping of the cord 12 from the opening 36 to at least one of the openings 38 also helps to retain the cord 12 at the rear of the earplug 10.

FIGS. 6 and 6a illustrates an alternative structure for this second embodiment. In particular as shown in dotted line in FIG. 6 and in full line in the side view in FIG. 6a, the opening 36 may be eliminated and replaced by a post 37 extending outward from the handle 34. Further in place of the opening 36, cutout areas 39 maybe formed on opposite sides of the handle and with the cutout areas extending from the slot openings 38 to form a pathway for the cord 12 between the slot openings and around the post 37. The post 37 may include an enlarged to portion 41 to ensure that the cord 12 is held in position as the cord 12 is pulled into the slot openings 3 to frictionally engage the slot openings 38 in a manner similar to that shown in FIG. 5.

FIG. 7 illustrates another embodiment of the cord attachment apparatus of the present invention. The handle portion 34 of FIG. 7 includes a first opening 40 passing through a flange 42 extending outward from the handle portion. The handle portion also includes an opening 44 formed as an open slot. The opening 44 may include ridges as shown. As can be seen in FIG. 7, the cord 12 may be passed through the opening 40 and with an end portion of the cord then pushed into the open slot opening 44 to secure the cord to the handle portion. In particular, the opening 44 is smaller in cross-section than the cord 12 so that the cord, when passed through the opening 40 and pushed into the opening 44, the cord 12 is held in the openings 44 by friction. The combination of the change in direction or looping of the cord 12 from the opening 40 to the opening 44 also helps to retain the cord 12 at the rear of the earplug 10.

FIG. 8 illustrates a further embodiment of the cord attachment apparatus of the present invention. The handle portion 34 of FIG. 8 includes a hinged portion 46 extending outward from the handle portion. The hinge itself may be a living hinge 48. The handle portion also includes a first vertical opening 50 extending into the handle portion 34. The hinged portion 46 includes a boss member 52 and with a second opening 54 extending through the boss 52. The boss member 52 includes slots 56. The second opening 54 thereby extends through the hinged portion 46 and the slots 56 allow the opening 54 to be made smaller as will be shown.

As can be seen in FIGS. 9*a* and 9*b*, the cord 12 may be passed through the opening 54 and a small end portion of the cord extends outward as shown in FIG. 9*a*. The hinged portion 46 is then rotated about the living hinge 48 so that the boss 52 and the small end portion of the cord 12 is inserted then into the opening 50 as shown in FIG. 9*b*. The opening 50 is smaller in cross-section than the outside cross-section of the boss 52 so that as the boss enters the opening 50, the opening 54, through the boss 52, is reduced in cross-section as the slots 56 in the boss 52 are forced together. Thereby the cord 12, when passed through the opening 54 and then pushed into the opening 50, is held in the opening 54 by friction as the slots 56 of the boss 52 are forced together.

Generally in each embodiment of the invention, an end portion of the cord is first passed through a first opening that is larger than the outside cross-section of the cord so that the cord need not have a stiff end portion and can thereby be a pliable plastic or a pliable braided material. The end portion of the cord is then easily inserted into a second opening and held in this second opening by friction. This can occur pulling the cord through a slot as shown by the embodiments of FIGS. 1-3 and 6 or pushing the cord into a slot or opening as shown by the embodiments of FIGS. 7 and 8.

The present invention produces a corded earplug, where the cord is securely attached to the ends of the earplugs. This attachment method and structure is simple and eliminates the difficulties of the prior art of applying an adhesive and then inserting the cord into the end of an earplug during the short time that the adhesive is liquid. The method shown in the present invention provides for an extremely strong attachment between the cord and the end of the earplug yet allowing the removal of the cord if desired.

Although the invention has been described with reference to particular embodiments, it should be appreciated that various adaptations and modifications may be made and the invention is only to be limited by the appended claims.

The invention claimed is:

1. A method of making a corded earplug, including the following steps,
   providing a flexible cord material and with the cord material having a first cross-section,
   providing an earplug having a nose portion for insertion into the ear and a handle portion extending from the nose portion and lying outside of the ear when the nose portion is inserted into the ear,
   providing the handle portion with at least first and second openings physically displaced from each other and with the first opening extending within a portion of the handle portion and with the second opening extending within a portion of the handle portion and having a second cross-section smaller than the first cross-section of the cord material to provide for a difference in cross-section between the cord material and the second opening,
   inserting an end portion of the flexible cord material into the first opening extending within the handle portion, and
   inserting the end portion of the flexible cord material into the second opening in the handle portion after the end portion of the flexible cord material has been inserted into the first opening extending within the handle portion to have the end portion of the flexible cord material frictionally engaged in the second opening along its length to lock the flexible cord material to the handle portion of the earplug because of the difference in cross-section between the cord material and the second opening because the second cross-section of the second opening is smaller than the first cross-section of the cord material.

2. The method of claim 1 wherein the second opening in the handle portion that receives the end portion of the flexible cord material with frictional engagement is provided as a slot to receive the cord material.

3. The method of claim 2 wherein the second opening in the handle portion receives the end portion of the flexible cord material with frictional engagement by pulling the cord material into the slot.

4. The method of claim 2 wherein the second opening in the handle portion receives the end portion of the flexible cord material with frictional engagement by pushing the cord material into the slot.

5. The method of claim 1 wherein the first and second openings are physically displaced from each other and are also angularly displaced from each other.

6. The method of claim 1 wherein the first opening extending within the handle portion is provided as a slot that extends across the handle to receive the cord material.

7. The method of claim 1 wherein both the first and second openings are provided as a slot that extends across the handle to receive the cord material.

8. The method of claim 1 wherein the first opening extending within the handle portion is provided as a slot that extends across the handle to receive the cord material and a pair of second openings is provided each as a slot that is angularly displaced from the first opening to receive the cord material and with the first opening extending within the handle portion to initially receive the cord material and with the inserting of the cord material into the pair of second openings to have the cord material frictionally engaged within the second openings by pulling the cord material into the pair of second openings.

9. The method of claim 1 wherein the first and second openings are physically displaced from each other and are also angularly inline and coaxial with each other.

10. The method of claim 1 wherein the first and second openings are angularly inline and coaxial with each other and with both the first and second openings formed as a boss member initially having the first opening there-through and with the boss member initially having a first outer cross-section and with a third opening in the handle portion for receiving the boss member and the third opening having a second inner cross-section smaller and different than the first outer cross-section in the boss member and with the cord material initially inserted through the first opening in the boss member and with the boss member with the cord material then inserted into the third opening to compress and form the second opening in the boss member because of the difference in cross-sections between the first outer cross-section of the boss member and the second inner cross-section of the third opening to frictionally engage the cord material.

11. A corded earplug, including the following,
   a flexible cord material and with the cord material having a first cross-section, an earplug having a nose portion for insertion into the ear and a handle portion extending from the nose portion and lying outside of the ear when the nose portion is inserted into the ear, the handle portion including at least first and second openings physically displaced from each other and with first opening extending within the handle portion and with the second opening extending within the handle portion and having a second cross-section smaller than the cross-section of the cord material to provide for a difference in cross-section between the cord material and the second opening, an end portion of the flexible cord material for insertion into the first opening extending within the handle portion, and the end portion of the flexible cord material may be inserted into the second opening in the handle portion after the end portion of the flexible cord material has been inserted into the first opening extending within the handle portion and thereby has the end portion of the flexible cord material frictionally engaged along its length to lock the flexible cord material to the handle portion of the earplug because of the difference in cross-section between the cord material and the second opening because the second cross-section of the second opening is smaller than the first cross-section of the cord material.

12. The corded earplug of claim 11 wherein the second opening in the handle portion that receives the end portion of the flexible cord material with frictional engagement is provided as a slot to receive the cord material.

13. The corded earplug of claim 12 wherein the second opening in the handle portion receives the end portion of the flexible cord material with frictional engagement as the cord by pulling the cord material into the slot.

14. The corded earplug of claim 12 wherein the second opening in the handle portion receives the end portion of the flexible cord material with frictional engagement by pushing the cord material into the slot.

15. The corded earplug of claim 11 wherein the first and second openings are physically displaced from each other and are also angularly displaced from each other.

16. The corded earplug of claim 11 wherein the first opening extending within the handle portion is provided as a slot that extends across the handle to receive the cord material.

17. The corded earplug of claim 11 wherein both of the first and second openings are provided as a slot that extends across the handle to receive the cord material.

18. The corded earplug of claim 11 wherein the first opening extending within the handle portion is provided as a slot that extends across the handle to receive the cord material and a pair of second openings is provided each as a slot that is angularly displaced from the first opening to receive the cord material and with the first opening extending within the handle portion to initially receive the cord material and with the inserting of the cord material into the pair of second openings having the cord material frictionally engaged within the second openings when the cord material is pulled into the pair of second openings.

19. The corded earplug of claim 11 wherein the first and second openings are physically displaced from each other and are also angularly inline and coaxial with each other.

20. The corded earplug of claim 11 wherein the first and second openings are angularly inline and coaxial with each other and with both first and second openings formed as a boss member initially having the first opening there-within and with the boss member initially having a first outer cross-section and with a third opening in the handle portion for receiving the boss member and having a second inner cross-section smaller and different than the first cross-section in the boss member and with the cord material initially inserted within the first opening in the boss member and when the boss member with the cord material is then inserted into the third opening this compresses the boss member to form the second opening in the boss member because of the difference in cross-sections between the second outer cross-section of the boss member and the first inner cross-section of the third opening to frictionally engage the cord material.

* * * * *